United States Patent [19]
Burgess et al.

[11] Patent Number: 5,811,080
[45] Date of Patent: Sep. 22, 1998

[54] PROCESS FOR INCREASED FLAVOR IMPACT IN ORAL CARE PRODUCTS

[75] Inventors: Steven Carl Burgess, Sharonville; James Grigg Upson, Springdale; Lowell Alan Sanker, Cincinnati, all of Ohio

[73] Assignee: The Procter & Gamble Company, Cincinnati, Ohio

[21] Appl. No.: 756,450

[22] Filed: Nov. 26, 1996

[51] Int. Cl.[6] .................... A61K 7/16; A61K 7/18; A61K 7/20

[52] U.S. Cl. ................... 424/53; 424/49; 424/52; 424/57

[58] Field of Search .......................... 424/49–58

[56] References Cited

U.S. PATENT DOCUMENTS

| | | | |
|---|---|---|---|
| 3,620,979 | 11/1971 | Curliss et al. | 252/385 |
| 3,928,560 | 12/1975 | Neely et al. | 424/52 |
| 3,959,510 | 5/1976 | Felton et al. | 426/540 |
| 4,003,971 | 1/1977 | Mannara | 264/9 |
| 4,508,744 | 4/1985 | Kruger et al. | 426/590 |
| 4,824,649 | 4/1989 | Shyu | 423/314 |
| 4,873,068 | 10/1989 | Hensler | 423/305 |
| 4,906,490 | 3/1990 | Bakal et al. | 426/603 |
| 4,925,655 | 5/1990 | Smigel et al. | 424/52 |
| 4,945,087 | 7/1990 | Talwar et al. | 514/60 |
| 4,997,634 | 3/1991 | Hensler | 423/305 |
| 4,997,638 | 3/1991 | Buckholtz | 423/314 |
| 5,085,850 | 2/1992 | Pan et al. | 424/49 |
| 5,149,521 | 9/1992 | Hirose et al. | 424/58 |
| 5,202,111 | 4/1993 | Spaltro et al. | 424/49 |
| 5,256,402 | 10/1993 | Prencipe et al. | 424/53 |
| 5,292,502 | 3/1994 | Burke et al. | 424/54 |
| 5,296,215 | 3/1994 | Burke et al. | 424/49 |
| 5,310,563 | 5/1994 | Curtis et al. | 424/616 |
| 5,372,803 | 12/1994 | Williams et al. | 424/53 |
| 5,403,578 | 4/1995 | Gordon | 424/53 |
| 5,424,059 | 6/1995 | Prencipe et al. | 424/52 |
| 5,456,902 | 10/1995 | Williams et al. | 424/49 |
| 5,456,903 | 10/1995 | Huetter et al. | 424/57 |
| 5,496,541 | 3/1996 | Cutler | 424/50 |
| 5,565,190 | 10/1996 | Santalucia et al. | 424/53 |
| 5,571,501 | 11/1996 | Toy | 424/49 |
| 5,624,906 | 4/1997 | Vermeer | 514/23 |

FOREIGN PATENT DOCUMENTS

| | | | |
|---|---|---|---|
| 2162812 | 5/1996 | Canada | A61K 7/20 |
| 2162821 | 5/1996 | Canada | A61K 7/20 |
| 2162885 | 5/1996 | Canada | A61K 7/20 |
| 0 712 624 A2 | 5/1996 | European Pat. Off. | A61K 7/16 |
| 2079325 | 1/1996 | Spain | A61K 7/28 |

*Primary Examiner*—Shep K. Rose
*Attorney, Agent, or Firm*—Angela Marie Stone; Mary Catherine Hentz; Douglas C. Mohl

[57] ABSTRACT

The method of manufacturing comprises the steps of: (a) preparing a mixture of a favor system, one or more humectants, and one or more aqueous carrier materials; (b) adding tetrasodium pyrophosphate and calcium peroxide, all at once or in portions, under conditions wherein less than about 20% of the total pyrophosphate and calcium peroxide are dissolved in the mixture; and wherein further any remaining aqueous carrier materials not added to the mixture during step (a) are added in whole or in part in step (b) or thereafter, either by themselves or with any remaining amount of the tetrasodium pyrophosphate or calcium peroxide, under conditions such that less than about 20% of the total pyrophosphate and calcium peroxide are dissolved in the mixture; (c) heating the mixture to a temperature range of from about 38° C. (100° F.) to about 71° C. (160° F.) and preferably to a temperature range of from about 52° C. (125° F.) to about 57° C. (135° F.), and (d) homogenizing the mixture in the temperature range for about 15 minutes to about 60 minutes. The tetrasodium pyrophosphate salt and peroxide are two of the last components to be added to the mixture, preferably after all or much of the other sodium-containing salts present in the composition have been added to the process mixture. By these methods, the dissolved tetrasodium pyrophosphate salt is less likely to recrystalize in the form of glass-like crystal particles of tetrasodium pyrophosphate decahydrate.

14 Claims, No Drawings

PROCESS FOR INCREASED FLAVOR IMPACT IN ORAL CARE PRODUCTS

BACKGROUND OF THE INVENTION

In recent years, the dentifrice products have been developed to include tartar control agents, baking soda, peroxides, and antibacterial agents. Although each of these ingredients brings an added benefit to the dentifrice, it may also bring additional cost. Despite these many advances in dentifrice formulations in recent years, there is still a need for improved products and products that can be made cost effectively. The present inventors have discovered a method which reduces the amount of flavor required by about 10% while still achieving the same flavor impact as a dentifrice made with the same flavor, but by a different method. The method requires heating the mixture to a specified temperature range once all of the ingredients have been added and then homogenizing this mixture while it is at the specified temperature range. The benefit of being able to use 10% less flavor and still achieve the same flavor impact would not have been expected to one skilled in the art. It is generally known that when a mixture is heated and/or homogenized, the flavor components and other volatile materials may be lost due to vaporization or evaporation. Therefore, it would generally be expected that this method would reduce the impact of the flavor, rather than increase the flavor impact. The inventors have also discovered that the method may be used to make a dentifrice containing a variety of different ingredients.

It is an object of the present invention to provide a method for manufacturing a dentifrice composition comprising about 10% less of a flavor system. A further object of the present invention is to provide compositions which comprise a variety of optional oral care ingredients, such as baking soda, peroxide, tartar control ingredients, xylitol, and fluoride. It is also an object of the present invention to provide a method of manufacturing which reduces the total cost of a dentifrice formulation.

These and other objects of the present invention will become readily apparent from the detailed description which follows.

All percentages and ratios used herein are by weight of the total composition, and all measurements are made at 25° C., unless otherwise specified.

SUMMARY OF THE INVENTION

The present invention relates to a method of manufacturing a dentifrice composition comprising the steps of preparing a mixture of a flavor system, one or more humectants, and one or more aqueous carriers; heating the mixture to a temperature range of from about 38° C. to about 71° C.; and homogenizing the mixture in the temperature range for about 15 minutes to about 60 minutes; wherein the dentifrice composition has a total water content of from about 5% to about 20%.

DETAILED DESCRIPTION OF THE INVENTION

The oral compositions of the present invention may be in the form of a toothpaste or dentifrice. The term "dentifrice", as used herein, means paste, gel, or liquid formulations unless otherwise specified. The dentifrice may be in any desired form, such as deep striped, surface striped, multilayer, having the gel surrounding the paste, or any combination thereof. The dentifrice may also be a multilayer composition which is extruded from the tube in combination paste/gel stripes.

The term "oral composition" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

The term "aqueous carrier" as used herein means any safe and effective materials for use in the compositions of the present invention. Such materials include fluoride ion sources, pyrophosphate source, peroxide source, alkali metal bicarbonate salt, xylitol, thickening materials, humectants, water, buffering agents, abrasive polishing materials, surfactants, titanium dioxide, sweetening agents, coloring agents, and mixtures thereof.

The present compositions comprise essential components, as well as optional components. The essential and optional components of the compositions of the present invention are described in the following paragraphs.

FLAVOR SYSTEM

The present composition includes a flavor system. The components of the flavor system may be in the form of an oil, liquid, semi-solid, solid, or powder and may be of a natural and/or synthetic flavor origin. Various flavors can be used in the flavor system of the present invention. The flavor system generally consists of flavor components from the group consisting of peppermint, spearmint, cinnamon, spice, wintergreen, fruit, citrus, herbal, medicinal, and common food flavors (i.e. chocolate) and mixtures thereof. Illustrative, but nonlimiting examples of such components include peppermint oils such as Mentha piperita and Mentha spearmint oils such as Mentha cardiaca and Mentha spicata; hydrocarbons such as limonene, caryophyllene, myrcene, and humulene; alcohols such as menthol, linalool, 3-decanol, and pinocarveol; ketones such as peperitone, menthone, spicatone, and 1-carvone; aldehydes such as acetaldehyde, 3-hexanal, or n-octanal; oxides such as menthofuran, pepertione oxide, or carvyl acetate-7,7 oxide; acids such as acetic and ocenoic; and sulphides such as dimethyl sulphide. Components also include esters such as menthyl acetate, benzyl isobutyrate, and 3-octyl acetate. The esters are stable in compositions having a pH of about 7 or lower, and preferably a pH of about 4.5 or lower. The components may also consist of essential oils such sage oil, parsley oil, marjoram oil, cassia oil, clove bud oil, cinnamon oil, eucalyptus oil, anise oil, and mixtures thereof. The flavor components may also consist of flavor chemicals such as cinnamic aldehyde, eugenol, ionone, anethole, eucalyptol, methyl salicylate, oxanone, alpha-irisone, and mixtures thereof. Preferred are peppermint oils, spearmint oils, menthol, anethole, methyl salicylate, cinnamon oils, clove bud oils, oxanone, and mixtures thereof. Flavor components are described in more detail in Fenaroli's *Handbook of Flavor Ingredients*, Third Edition, Volumes 1 & 2, CRC Press, Inc. (1995), and Steffen Arctander's *Perfume and Flavor Chemicals*, Volumes 1 & 2, (1969). The flavor system may additionally comprise components such as vanillin, ethyl vanillin, heliotropine, propenyl guaethol, vanilla extracts, veratraldehyde, 4-cis-heptenal, diacetyl, butyl lactate, ethyl lactate, methyl-para-tert-butyl phenyl acetate, gamma and delta hexalactone and heptalactone, benzodihydropyrone, butter starter distillate, delta tetradecalactone, butyraldehyde, and mixtures thereof. A coolant may also be incorporate into the flavor system. The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, (known commercially as "WS-3"") and mixtures thereof. The flavor system is used in the present composition at levels of from about 0.1% to about 10%, preferably from about 0.5% to about 5%, and most preferably from about 0.8% to about 2%, by weight of the composition.

HUMECTANTS

Another component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, other edible polyhydric alcohols, poloxamers (sold under trade name Pluronic), and combination thereof. Polyethylene glycols are one of the preferred humectants. Polyethylene glycols useful herein are those which are liquids at room temperature or have a melting point slightly there above. Liquid and low-melting polyethylene glycols are commercially available from Union Carbide under the Carbowax® tradename. Preferred are those polyethylene glycols having a molecular weight range of from about 200 to about 2000 and corresponding n values of from about 4 to about 40. More preferred are polyethylene glycols having a molecular weight range of from about 400 to about 1600. The total amount of humectant generally comprises from about 0.5% to 70%, preferably from about 5% to 60%, and more preferably from about 15% to about 55%, by weight of the compositions herein.

TOTAL WATER CONTENT

Water is also contained in the present invention. Water used in the preparation of these compositions should preferably be of low ion content and free of organic impurities. The "total water content" of the composition, as used herein, includes the free water which is added plus the water which is introduced with other materials, such as with sorbital, silica, color solutions, or surfactant solutions. The total water content of the present invention is from about 5% to about 20%, preferably from about 7% to about 14%, more preferably from about 9% to about 12%, and most preferably from about 10% to about 11%, by weight of the composition.

AQUEOUS CARRIERS

In preparing the present compositions, it is desirable to add one or more aqueous carriers to the compositions. Aqueous carriers contain materials that are well known in the art and readily chosen by one skilled in the art based on the physical and aesthetic properties desired for the compositions being prepared. Aqueous carriers typically comprise from about 90% to about 99.9%, preferably from about 95% to about 99.5%, and more preferably from about 98% to about 99.2%, by weight of the total composition.

FLUORIDE ION SOURCE

The present invention may also incorporate a soluble fluoride source capable of providing free fluoride ions. Preferred soluble fluoride ion sources include sodium fluoride, stannous fluoride, indium fluoride, and sodium monofluorophosphate. Sodium fluoride is the most preferred soluble fluoride ion source. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others. Both patents are incorporated herein by reference in their entirety.

The present compositions contain a soluble fluoride source capable of providing from about 50 ppm to about 3500 ppm, and preferably from about 500 ppm to about 3000 ppm of free fluoride ions.

PYROPHOSPHATE SOURCE

The present invention may also include a pyrophosphate ion source which is from a pyrophosphate salt. The pyrophosphate salts useful in the present compositions include the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%, by weight of the composition. Free pyrophosphate ions may be present in a variety of protonated states depending on a the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 3% to about 8%, by weight of the composition. Some or all of the tetrasodium pyrophosphate is undissolved in the product and is present as tetrasodium pyrophosphate particles. Pyrophosphate ions in different protonated states (e.g., $HP_2O_7^{-3}$) may also exist depending upon the pH of the composition and if part of the tetrasodium pyrophosphate is dissolved.

Compositions may also comprise a mixture of dissolved and undissolved pyrophosphate salts. Any of the above mentioned pyrophosphate salts may be used.

The pyrophosphate salts are described in more detail in Kirk & Othmer, *Encyclopedia of Chemical Technology*, Third Edition, Volume 17, Wiley-Interscience Publishers (1982), incorporated herein by reference in its entirety, including all references incorporated into Kirk & Othmer.

Optional agents to be used in place of or in combination with the pyrophosphate salt include such materials known to be effective in reducing calcium phosphate mineral deposition related to calculus formation. Agents included are synthetic anionic polymers [including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS)], zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

PEROXIDE SOURCE

The present invention may include a peroxide source. The peroxide source is selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the composition.

ALKALI METAL BICARBONATE SALT

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 50%, preferably from about 0.5% to about 30%, more preferably from about 0.5% to about 15%, and most preferably from about 0.8% to about 2% of an alkali metal bicarbonate salt, by weight of the composition.

XYLITOL

The present invention may also include xylitol. Xylitol is a sugar alcohol that is used as a sweetener or humectant. Xylitol may provide a therapeutic effect, such as an antibacterial or anticaries effect. The present compositions typically comprise xylitol at a level from about 0.01% to about 25%, preferably from about 3% to about 15%, more preferably from about 5% to about 12%, and most preferably from about 9% to about 11%, by weight of the composition.

ADDITIONAL AQUEOUS CARRIERS

The present invention compositions in the form of toothpastes, typically contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the composition.

The pH of the present compositions is preferably adjusted through the use of buffering agents. Buffering agents, as used herein, refer to agents that can be used to adjust the pH of the compositions to a range of about pH 6.5 to about pH 10.5. The compositions may contain a high pH range of from about 9.0 to about 10.5. These agents include monosodium phosphate, trisodium phosphate, sodium hydroxide, sodium carbonate, citric acid, and sodium citrate. Buffering agents can be used at a level of from about 0.5% to about 10%, by weight of the present compositions.

An abrasive polishing material may also be included in the toothpaste compositions. The abrasive polishing material contemplated for use in the compositions of the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al in U.S. Pat. No. 3,070,510, issued Dec. 25, 1962, incorporated herein by reference. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica xerogels marketed under the trade name "Syloid" by the W. R. Grace & Company, Davison Chemical Division. Also preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, incorporated herein by reference. Suitable abrasives also include the silica abrasives described in U.S. pat. application Ser. Nos., 08/434,147 and 08/434,149, both filed May 2, 1995, herein incorporated by reference. The abrasive in the toothpaste compositions described herein is generally present at a level of from about 6% to about 70% by weight of the composition. Preferably, toothpastes contain from about 10% to about 50% of abrasive, by weight of the composition.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977, incorporated herein by reference in its entirety. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the compositions.

Coloring agents may also be added to the present composition. The coloring agent may be in the form of an aqueous solution, preferably 1% coloring agent in a solution of water. Color solutions generally comprise from about 0.01% to about 5%, by weight of the composition.

Sweetening agents can be added to the compositions. These include sodium saccharin, dextrose, sucrose, chlorinated sucrose, lactose, maltose, levulose, aspartame, sodium cyclamate, D-tryptophan, dihydrochalcones, acesulfame, monoammonium glycyrrhizinate, and mixtures thereof. Sweetening agents are generally used in toothpastes at levels of from about 0.005% to about 5%, by weight of the composition.

The present invention may also include other agents. Included among such agents are water insoluble non-cationic agents such as triclosan and other agents of the type disclosed in Parran, Jr. et al., U.S. Pat. No. 5,015,466, issued May 14, 1991, incorporated by reference herein in its entirety.

The composition can be in the form of a multilayer toothpaste composition. This composition may comprise two or more separate layers which are in contact with each other. The separate layers may be a paste and a gel that when extruded from the tube, appear as combination paste/gel stripes. One of the layers must comprise all of the essential components, while the other layers may contain less than all of the essential components or may be any dentifrice formulation. Alternatively, dentifrice compositions can be physically separated in a dentifrice dispenser. The dispenser may be a tube, pump, or any other container suitable for dispensing toothpaste. Dual compartment packages suitable for this purpose are described in U.S. Pat. No. 4,528,180, issued Jul. 9, 1985; U.S. Pat. No. 4,687,663, issued Aug. 18, 1987; and U.S. Pat. No. 4,849,213, issued Jul. 18, 1989, all to Shaeffer, all incorporated herein in their entirety. The dispenser will deliver approximately equal amounts of each dentifrice composition through an opening. The compositions may intermix once dispensed. Alternatively, the oral formulation may be delivered from a kit containing two separate dispensers which are used to deliver two dentifrice compositions that are both used simultaneously.

METHOD OF MANUFACTURING

Toothpaste compositions of the present invention are prepared by the following methods. If the present composition does not contain a pyrophosphate salt or contains predominately dissolved pyrophosphate salt, the method of manufacturing comprises the steps of: (a) preparing a mixture of a flavor system, one or more humectants, and one or more aqueous carrier materials, (b) heating the mixture to a temperature range of from about 38° C. (100° F.) to about 71° C. (160° F.) and preferably to a temperature range of from about 52° C. (125° F.) to about 57° C. (135° F.), and (c) homogenizing the mixture in the temperature range for about 15 minutes to about 60 minutes.

If the present composition contains predominately undissolved pyrophosphate salt, the method of manufacturing comprises the steps of: (a) preparing a mixture of a flavor system, one or more humectants, and one or more aqueous carrier materials; (b) adding tetrasodium pyrophosphate, all at once or in portions, under conditions whereby less than about 20% of the total pyrophosphate is dissolved in the dentifrice mixture; and wherein further any remaining aqueous carrier materials not added to the mixture during step (a) are added in whole or in part in step (b) or thereafter, either by themselves or with any remaining amount of the tetrasodium pyrophosphate, under conditions such that less than about 20% of the total pyrophosphate is dissolved in the mixture; (c) heating the mixture to a temperature range of from about 38° C. (100° F.) to about 71° C. (160° F.) and preferably to a temperature range of from about 52° C. (125° F.) to about 57° C. (135° F.), and (d) homogenizing the mixture in the temperature range for about 15 minutes to about 60 minutes. Preferably, the amount of pyrophosphate dissolved in the mixture for the methods and compositions of the present invention is less than about 10% by weight of the total pyrophosphate present in the compositions.

If the present composition contains predominately undissolved pyrophosphate salt and a peroxide source, the method of manufacturing comprises the steps of: (a) preparing a mixture of a flavor system, one or more humectants, and one or more aqueous carrier materials; (b) adding tetrasodium pyrophosphate and calcium peroxide, all at once or in portions, under conditions wherein less than about 20% of the total pyrophosphate and calcium peroxide are dissolved in the mixture; and wherein further any remaining aqueous carrier materials not added to the mixture during step (a) are added in whole or in part in step (b) or thereafter, either by themselves or with any remaining amount of the tetrasodium pyrophosphate or calcium peroxide, under conditions such that less than about 20% of the total pyrophosphate and calcium peroxide are dissolved in the mixture; (c) heating the mixture to a temperature range of from about 38° C. (100° F.) to about 71° C. (160° F.) and preferably to a temperature range of from about 52° C. (125° F.) to about 57° C. (135° F.), and (d) homogenizing the mixture in the temperature range for about 15 minutes to about 60 minutes. The amount of pyrophosphate dissolved in the mixture for the methods and compositions of the present invention is preferably less than about 10% by weight of the total pyrophosphate present in the compositions and the amount of calcium peroxide dissolved in the mixtures is preferably less than about 10% by weight of the total amount of calcium peroxide present in the compositions.

Preferably, one or more of the following process conditions are controlled as follows to limit the solubility of the tetrasodium pyrophosphate and calcium peroxide in the dentifrice mixture: (1) the neat pH of the mixture is above about pH 8, preferably above about pH 9, during and after the tetrasodium pyrophosphate and calcium peroxide additions are made to the mixture; and (2) the tetrasodium pyrophosphate salt and peroxide are two of the last components to be added to the mixture, preferably after all or much of the other sodium-containing salts present in the composition have been added to the process mixture. By these methods, the dissolved tetrasodium pyrophosphate salt is less likely to recrystalize in the form of glass-like crystal particles of tetrasodium pyrophosphate decahydrate and the peroxide is less likely to breakdown and react with the fluoride to form calcium fluoride.

During the method of manufacturing, the mixture is heated to a temperature range of about 38° C. (100° F.) to about 71° C. (160° F.) and preferably to a temperature range of from about 52° C. (125° F.) to about 57° C. (135° F.). One or more heating variables may be controlled during this method. The heating variables include: the rate of heating the mixture to the temperature range and the rate of cooling the mixture from the temperature range. The amount of time that the mixture is homogenized while in the temperature range is for about 15 minutes to about 60 minutes. Preferably, this amount of time is from about 20 minutes to about 40 minutes. Additionally, the rate of speed of the homogenization may also be controlled. The desired speed will depend upon the size of equipment and the size of the mixture being made, among other variables.

METHOD OF TREATEMENT

The present invention compositions additionally relate to a method for reducing plaque on dental enamel. The method of treatment herein comprises contacting the dental enamel surfaces in the mouth with the oral compositions according to the present invention.

The following examples further describe and demonstrate embodiments within the scope of the present invention. These examples are given solely for the purpose of illustration and are not to be construed as limitations of the present invention as many variations thereof are possible without departing from the spirit and scope.

EXAMPLE I

| Ingredient | Weight % |
| --- | --- |
| Sorbitol(a) | 48.767 |
| Glycerin | 10.000 |
| Water | 12.340 |
| Sodium Fluoride | 0.243 |

-continued

| | |
| --- | --- |
| Sodium Saccharin | 0.400 |
| Monosodium Phosphate | 0.500 |
| Trisodium Phosphate | 1.500 |
| Xanthan Gum | 0.400 |
| Carbopol | 0.300 |
| Titanium Dioxide | 0.500 |
| Color Solution | 0.050 |
| Silica | 20.000 |
| Sodium Alkyl Sulfate(c) | 4.000 |
| Flavor System | 1.000 |

| Flavor System | Weight % of Flavor System |
| --- | --- |
| Peppermint | 64.000 |
| Anethole | 10.000 |
| Dairy-creme Flavor | 5.000 |
| Cinnamon Oil | 8.000 |
| Clove Bud Oil | 8.000 |
| Coolant | 5.000 |

Example I is prepared as follows. Start by combining water and sorbitol. Mix thoroughly and add sodium fluoride, saccharin, and the phosphates. Next add the silica. Disperse the thickening agents, xanthan gum and carbopol, in the remaining humectant, glycerin, before adding to the mixture. Lastly, add the flavor system, color solution, titanium dioxide, and surfactant, sodium alkyl sulfate. Continue mixing, heat the mixture to a temperature range of from about 44° C. to about 71° C., and homogenize the mixture for approximately 30 minutes. Allow the mixture to cool, then mill and/or deareate the final product if desired for aesthetic preference.

EXAMPLE II

| Ingredient | Weight % |
| --- | --- |
| Sorbitol(a) | 36.240 |
| Glycerin | 10.000 |
| Water | 10.217 |
| Sodium Fluoride | 0.243 |
| Sodium Saccharin | 0.500 |
| Sodium Carbonate | 1.500 |
| Sodium Bicarbonate | 24.000 |
| Carboxymethylcellulose | 1.000 |
| Titanium Dioxide | 0.500 |
| Silica | 11.000 |
| Sodium Alkyl Sulfate(c) | 4.000 |
| Flavor System | 0.800 |

| Flavor System | Weight % of Flavor System |
| --- | --- |
| Peppermint | 10.000 |
| Spearmint Oil | 50.000 |
| Menthol | 25.000 |
| Anethole | 10.000 |
| Coolant | 5.000 |

Example II is prepared as follows. Start by combining water and sorbitol. Mix thoroughly and add sodium fluoride and saccharin. Next add the sodium carbonate, sodium bicarbonate, and then the silica. Disperse the thickening agents, carboxymethylcellulose, in the remaining humectant, glycerin, before adding to the mixture. Lastly, add the flavor system, titanium dioxide, and surfactant, sodium alkyl sulfate. Continue mixing, heat the mixture to a temperature range of from about 52° C. to about 57° C., and homogenize the mixture for approximately 20 to 45 minutes. Allow the mixture to cool, then mill and/or deareate the final product if desired for aesthetic preference.

EXAMPLE III

| Ingredient | Weight % |
| --- | --- |
| Sorbitol[a] | 23.904 |
| Glycerin | 8.501 |
| Water | 23.511 |
| Sodium Fluoride | 0.243 |
| Sodium Saccharin | 0.500 |
| Sodium Acid Pyrophosphate | 2.500 |
| Tetrasodium Pyrophosphate | 0.758 |
| Propylene Glycol 6 | 3.000 |
| Tetrapotassium Pyrophosphate[b] | 7.783 |
| Xanthan Gum | 0.450 |
| Carbopol | 0.300 |
| Titanium Dioxide | 0.500 |
| Color Solution | 0.050 |
| Silica | 22.000 |
| Sodium Alkyl sulfate[c] | 4.000 |
| Flavor System | 2.000 |

| Flavor System | Weight % of Flavor System |
| --- | --- |
| Peppermint | 5.000 |
| Menthol | 30.000 |
| Anethole | 3.000 |
| Dairy-creme Flavor | 2.000 |
| Orange Oil | 30.000 |
| Oxanone | 1.000 |
| Lemon Oil | 20.000 |
| WS-3 Coolant | 6.000 |
| Coolant | 3.000 |

Example III is prepared as follows. Start by combining water and sorbitol. Mix thoroughly and add sodium fluoride and saccharin. In the order listed, add sodium acid pyrophosphate, tetrasodium pyrophosphate, and tetrapotassium pyrophosphate. Next add the silica. Disperse the thickening agents, xanthan gum and carbopol, in the glycerin, before adding to the mixture. Add the polyethylene glycol. Lastly, add the flavor system, color solution, and surfactant, sodium alkyl sulfate. Continue mixing, heat the mixture to a temperature range of from about 52° C. to about 68° C., and homogenize the mixture for approximately 30 minutes. Allow the mixture to cool, then mill and/or deareate the final product if desired for aesthetic preference.

EXAMPLE IV

| Ingredient | Weight % |
| --- | --- |
| Sorbitol[a] | 13.611 |
| Glycerin | 15.000 |
| Water | 19.473 |
| Sodium Fluoride | 0.243 |
| Sodium Saccharin | 0.528 |
| Tetrasodium Pyrophosphate | 5.045 |
| Propylene Glycol 6 | 3.000 |
| Sodium Carbonate | 1.500 |
| Sodium Bicarbonate | 24.000 |
| Carboxymethylcellulose | 0.800 |
| Color Solution | 0.300 |
| Silica | 11.000 |
| Sodium Alkyl Sulfate[c] | 4.000 |
| Flavor System | 1.500 |

| Flavor System | Weight % of Flavor System |
| --- | --- |
| Peppermint | 30.000 |
| Spearmint Oil | 30.000 |
| Menthol | 25.000 |
| Anethole | 15.000 |

Example IV is prepared as follows. Start by combining water and sorbitol. Add sodium fluoride and saccharin. Add sodium carbonate. Next add the silica. The temperature of the mixture should be about 32° C. or less prior to the addition of sodium bicarbonate. Next, disperse the thickening agent, carboxymethylcellulose, in the glycerin, before adding to the mixture. Add the polyethylene glycol. Next add the flavor system, color solution, and surfactant, sodium alkyl sulfate. Lastly, slowly add the tetrasodium pyrophosphate. Continue mixing, heat the mixture to a temperature range of from about 38° C. to about 57° C., and homogenize the mixture for approximately 20 to 45 minutes. Allow the mixture to cool, then mill and/or deareate the final product if desired for aesthetic preference.

EXAMPLE V

| Ingredient | Weight % |
| --- | --- |
| Xylitol | 5.000 |
| Water | 26.500 |
| Saccharin | 0.400 |
| Sodium Fluoride | 0.243 |
| Glycerin | 23.561 |
| Polyethylene Glycol | 1.000 |
| Carboxymethylcellulose | 0.250 |
| Xanthan Gum | 0.600 |
| Sodium Bicarbonate | 2.500 |
| Sodium Carbonate | 1.250 |
| Tetrasodium pyrophosphate | 5.046 |
| Silica | 25.000 |
| Titanium Dioxide | 0.750 |
| Sodium alkyl sulfate[c] | 5.000 |
| Poloxamer 407 | 2.000 |
| Flavor System | 0.900 |

| Flavor System | Weight % of Flavor System |
| --- | --- |
| Peppermint | 55.000 |
| Spearmint Oil | 2.000 |
| Menthol | 20.000 |
| Anethole | 14.000 |
| Coolant | 9.000 |

Example V is prepared as follows. Start by combining water and enough glycerin to provide sufficient liquid for adequate mixing. Add xylitol and poloxamer to the mixture. Mix thoroughly and add sodium fluoride and saccharin. Add sodium carbonate. Next add the silica. The temperature of the mixture should be about 32° C. or less prior to the addition of sodium bicarbonate. Next, disperse the thickening agents, carboxymethylcellulose and xanthan gum, in the remaining glycerin, before adding to the mixtures. Add the polyethylene glycol. Next add the flavor system, titanium dioxide, and surfactant, sodium alkyl sulfate. Lastly, slowly add the tetrasodium pyrophosphate. Continue mixing, heat the mixture to a temperature range of from about 50° C. to about 71° C., and homogenize the mixture for approximately 30 minutes. Allow the mixture to cool, then mill and/or deareate the final product if desired for aesthetic preference.

EXAMPLE VI

| Ingredient | Weight % |
| --- | --- |
| Glycerin | 27.050 |
| Polyethylene Glycol 12 | 2.000 |
| Xanthan Gum | 0.300 |
| Carboxymethylcellulose | 0.200 |
| Water | 5.000 |
| Sodium Saccharin | 0.450 |
| Sodium Fluoride | 0.243 |
| Xylitol | 10.000 |
| Poloxamer 407 | 2.000 |

-continued

| | |
|---|---|
| Sodium Alkyl Sulfate(c) | 6.000 |
| Sodium Carbonate | 2.600 |
| Titanium Dioxide | 1.000 |
| Silica | 20.000 |
| Sodium Bicarbonate | 1.500 |
| Propylene Glycol | 15.011 |
| Tetrasodium Pyrophosphate | 5.046 |
| Calcium Peroxide | 0.500 |
| Flavor System | 1.100 |

| Flavor System | Weight % of Flavor System |
|---|---|
| Peppermint | 55.000 |
| Spearmint Oil | 2.000 |
| Menthol | 20.000 |
| Anethole | 12.500 |
| Dairy-creme Flavor | 2.500 |
| WS-3 Coolant | 8.000 |

(a)70% solution of sorbitol in water
(b)60% solution of tetrapotassium pyrophosphate in water
(c)27.9% solution of sodium alkyl sulfate in water Example VI is prepared as follows: Add approximately half of the glycerin to a mixing vessel. Disperse the thickening agents, carboxymethyl cellulose and xanthan gum, in the propylene glycol. Add this mixture of dispersed thickening agent in propylene glycol to the mixing vessel. Add the polyethylene glycol. Dissolve the sodium fluoride and sodium saccharin in water and add to the mixture. Add the xylitol and poloxamer. The flavor system and sodium alkyl sulfate are then added. Next, add the sodium carbonate, titanium dioxide, and the silica. Add the sodium bicarbonate. Disperse the tetrasodium pyrophosphate in the remaining glycerin and add to the mixture. Finally, add the calcium peroxide. Stir the mixture until homogeneous and then heat the mixture to a temperature range of from about 54° C. to about 55° C., and homogenize the mixture for approximately 30 to 45 minutes. Allow the mixture to cool, then mill and/or deareate the final product if desired for aesthetic preference.

What is claimed is:

1. A method of manufacturing predominately undissolved pyrophosphate and calcium peroxide dentifrice compositions comprising the steps of:
    a. preparing a mixture of a flavor system, one or more humectants, and one or more aqueous carriers;
    b. adding tetrasodium pyrophosphate and calcium peroxide, all at once or in portions, under conditions wherein less than about 20% of the total pyrophosphate and calcium peroxide are dissolved in the mixture, and wherein any further remaining aqueous carrier materials not added to the mixture during step (a) are added in whole or in part in step (b) or thereafter, either by themselves or with any remaining amount of the tetrasodium pyrophosphate or calcium peroxide under conditions such that less than about 20% of the total pyrophosphate and calcium peroxide are dissolved in the mixture;
    c. heating the mixture to a temperature range of from about 38° C. to about 71° C.; and
    d. homogenizing the mixture in the temperature range for about 15 minutes to about 60 minutes;
wherein the dentifrice composition has a total water content of from about 9% to about 20%.

2. The method of manufacturing a composition according to claim 1 wherein the tetrasodium pyrophosphate and calcium peroxide are added to the mixture after all other sodium-containing salts present in the composition have been added to the mixture.

3. The method of manufacturing a composition according to claim 2 wherein the mixture has a neat pH of above about pH 8 during and after the tetrasodium pyrophosphate and calcium peroxide additions are made to the mixture.

4. The method of manufacturing a dentifrice composition according to claim 3 wherein the one or more humectants are present in an amount of from about 0.5% to about 70%.

5. The method of manufacturing a dentifrice composition according to claim 4 wherein the flavor system is present in an amount of from about 0.1% to about 10%.

6. The method of manufacturing a dentifrice composition according to claim 5 wherein the humectants are selected from the group consisting of glycerin, sorbitol, polyethylene glycol, propylene glycol, other edible polyhydric alcohols, poloxamers, and combinations thereof.

7. The method of manufacturing a composition according to claim 6 wherein the tetrasodium pyrophosphate is in an amount of at least about 1.5%.

8. The method of manufacturing a composition according to claim 7 wherein the calcium peroxide is in an amount of from about 0.01% to about 5%.

9. The method of manufacturing a dentifrice composition according to claim 8 wherein a soluble fluoride ion source capable of providing from about 50 ppm to about 3500 ppm of free fluoride ions is added in step 10 (a).

10. The method of manufacturing a composition according to claim 9 wherein the soluble fluoride ion source is sodium fluoride.

11. The method of manufacturing a composition according to claim 10 wherein the composition has a neat pH of from about 9.0 to about 10.5.

12. The method of manufacturing a composition according to claim 11 wherein from about 0.5% to about 40% of an alkali metal bicarbonate salt is added in step 10 (a).

13. The method of manufacturing a composition according to claim 12 wherein from about from about 0.01% to about 25% of xylitol is added in step 10 (a).

14. The method of manufacturing a composition according to claim 13 wherein the aqueous carriers contain materials selected from the group consisting of thickening materials, water, buffering agents, surfactants, abrasive polishing materials, sweetening agents, coloring agents, titanium dioxide, and mixtures thereof.

* * * * *

UNITED STATES PATENT AND TRADEMARK OFFICE
CERTIFICATE OF CORRECTION

PATENT NO. : 5,811,080

DATED : September 22, 1998

INVENTOR(S) : Steven Carl Burgess, James Grigg Upson, Lowell Alan Sanker

It is certified that error appears in the above-identified patent and that said Letters Patent is hereby corrected as shown below:

Column 9, line 45, the word "TREATEMENT" should be --TREATMENT--

Signed and Sealed this

Sixteenth Day of March, 1999

Attest:

Q. TODD DICKINSON

Attesting Officer

Acting Commissioner of Patents and Trademarks